United States Patent
Li et al.

(10) Patent No.: US 10,575,729 B2
(45) Date of Patent: Mar. 3, 2020

(54) CONFOCAL LASER FUNDUS ANGIOGRAPHIC DEVICE

(71) Applicant: SUZHOU MICROCLEAR MEDICAL INSTRUMENTS CO., LTD., Suzhou, Jiangsu Province (CN)

(72) Inventors: Lei Li, Suzhou (CN); Enyi Zhao, Suzhou (CN); Xiaoping Hou, Suzhou (CN); Chaohong Li, Suzhou (CN)

(73) Assignee: SUZHOU MICROCLEAR MEDICAL INSTRUMENTS CO., LTD., Suzhou, JIangsu Province (CN)

( * ) Notice: Subject to any disclaimer, the term of this patent is extended or adjusted under 35 U.S.C. 154(b) by 19 days.

(21) Appl. No.: 15/768,543

(22) PCT Filed: May 17, 2017

(86) PCT No.: PCT/CN2017/084663
§ 371 (c)(1),
(2) Date: Apr. 14, 2018

(87) PCT Pub. No.: WO2018/040617
PCT Pub. Date: Mar. 8, 2018

(65) Prior Publication Data
US 2018/0303337 A1    Oct. 25, 2018

(30) Foreign Application Priority Data
Aug. 31, 2016    (CN) .......................... 2016 1 0775302

(51) Int. Cl.
*A61B 3/12*    (2006.01)
*A61B 3/00*    (2006.01)
(Continued)

(52) U.S. Cl.
CPC .............. *A61B 3/12* (2013.01); *A61B 3/0008* (2013.01); *A61B 3/1025* (2013.01); *A61B 3/156* (2013.01)

(58) Field of Classification Search
CPC ........... A61B 3/14; A61B 3/0025; A61B 3/12; A61B 3/102; A61B 3/0058
(Continued)

(56) References Cited

U.S. PATENT DOCUMENTS

| | | | |
|---|---|---|---|
| 7,198,367 B2* | 4/2007 | Akita | A61B 3/1233 351/206 |
| 2004/0263781 A1* | 12/2004 | Suzuki | A61B 3/14 351/206 |
| 2012/0218517 A1* | 8/2012 | Imamura | A61B 3/1241 351/206 |

FOREIGN PATENT DOCUMENTS

| | | |
|---|---|---|
| CN | 202837774 U | 3/2013 |
| CN | 202837775 U | 3/2013 |

(Continued)

*Primary Examiner* — Mohammed A Hasan
(74) *Attorney, Agent, or Firm* — Cheng-Ju Chiang

(57) ABSTRACT

A confocal laser fundus angiographic device, comprises: an objective lens, a scanning lens, a scanning galvanometer, a mirror, a filtering module, an imaging detection assembly and an excitation light source. The illumination light emitted by the excitation light source enters the fundus passing through the scanning galvanometer, the scanning lens and the objective lens. Fluorescent substances in fundus vessels are excited by the illumination light and emit light with a specific wavelength. The light with a specific wavelength enters the imaging detection assembly by passing through the objective lens, the scanning lens, the scanning galvanometer, the mirror and the filtering module. The filtering module comprises a base, a motor mounted on the base, a rotary block mounted on the motor and at least one filter mounted on the rotary block. The base is provided with a (Continued)

light-through hole. Compared with the prior art, the confocal laser fundus angiographic device is capable of automatically switching the filter, thereby avoiding the problem of forgetting to switch the filter due to the operator's mistake or switching the filter by mistake.

12 Claims, 5 Drawing Sheets

(51) Int. Cl.
  *A61B 3/10* (2006.01)
  *A61B 3/15* (2006.01)

(58) Field of Classification Search
  USPC ............................................. 351/206
  See application file for complete search history.

(56) References Cited

FOREIGN PATENT DOCUMENTS

| | | |
|---|---|---|
| CN | 202975566 U | 6/2013 |
| CN | 103750814 A | 4/2014 |
| CN | 103941521 A | 7/2014 |
| CN | 106214119 A | 12/2016 |
| CN | 106539556 A | 3/2017 |
| JP | H8-322798 A | 12/1996 |

* cited by examiner

CONFOCAL LASER FUNDUS ANGIOGRAPHIC DEVICE

CROSS-REFERENCE TO RELATED APPLICATIONS

This application claims priority to Chinese Application Serial No. 201610775302.5, filed Aug. 31, 2016, the disclosures of which are hereby incorporated by reference in their entirety.

TECHNICAL FIELD

The present invention generally relates to angiography imaging, and more particularly to a confocal laser fundus angiographic device.

BACKGROUND

Many eye diseases are associated with fundus changes, such as age-related macular degeneration (ARMD), diabetic retinitis, intraocular tumors, central serous chorioretinopathy (CSC), harada's disease and so on. Fundus fluorescein angiography and indocyanine green angiography are important diagnostic technique to inspect and record the condition of retina and choroidal vascular. In the 1960s, modern fundus fluorescein angiography began to be used in clinical medicine, and the indocyanine green angiography began to apply in clinical medicine in the mid-90s. It is of great significance to obtain accurate and clear fundus images to diagnosis and treat fundus diseases.

In the 1960s, modern fundus fluorescein angiography began to be used in clinical medicine, and the indocyanine green angiography began to apply in clinical medicine in the mid-90s. It is of great significance to obtain accurate and clear fundus images to diagnosis and treat fundus diseases.

The basic principle of fundus angiography are described as follows: intravenous injection of fluorescent substances as a contrast medium, when the fluorescent substances reaches the fundus blood vessel through the blood circulation, the fundus is irradiated with light can stimulate the fluorescent substances, and the fluorescent substances in the fundus blood vessel is excited to emit a specific wavelength fluorescence, the contrast machine records this fluorescence to get the image of the blood vessels in the eye.

The fundus angiographic device with a variety of imaging modes, such as: sodium fluorescein angiography, indocyanine green angiography, infrared fundus imaging, fundus self-fluorescence and so on. In order to filter out stray light, when the fundus angiographic device was switched between different imaging modes, we need to switch the filter corresponding to the imaging mode simultaneously. At present, when the operator is willing to switch the fundus angiographic device imaging mode, the operator has to manually switch the filter. The operator is likely to forget to switch the filter or switch the filter incorrectly due to a mistake, resulting in imaging failure.

In consideration of the above problems, there is a need to provide a confocal laser fundus angiographic device for automatic switching filter to solve the above problems.

SUMMARY OF INVENTION

Against the deficiency of the technology in existence, the aim of the present invention is to provide a confocal laser fundus angiographic device which is capable of automatically switching the filter, thereby avoiding the problem of forgetting to switch the filter due to the operator's mistake or switching the filter by mistake.

In order to solve the above technical problems, the technical scheme of the invention is realized as follows:

A confocal laser fundus angiographic device comprises an objective lens, a scanning lens, a scanning galvanometer, a mirror, a filtering module, an imaging detection assembly, and an excitation light source, the excitation light source emits illumination light passing through the scanning galvanometer, the scanning lens, the objective lens, and then entering in the fundus, the fluorescent substances in the fundus vein are excited by the illumination light to emit light with a specific wavelength, the light with the specific wavelength passes through the objective lens, the scanning lens, the scanning galvanometer, the mirror, the filtering module, and then enters in the imaging detection assembly, wherein the filtering module comprising a base, a motor mounted on the base, a rotary block mounted on the motor, and at least one piece of filter mounted on the rotary block, the base is provided with a light-through hole, the rotary block is a fan-shaped piece, the fan-shaped piece comprises a circular arc end and a top end. The top end is opposite to the circular arc end and it is provided with a mounting hole, the rotary block is mounted on the motor through the mounting hole, a blocking block is formed on outer side of the circular arc end facing away from the top end, a pair of limiting blocks are disposed on the base, the blocking block cooperates with the limiting blocks to limit a rotation angle of the rotary block, when the confocal laser fundus angiographic device in operation, the rotary block rotating under the driving of the motor to achieve that the filter and the light-through hole coincide.

As a preferred embodiment of the present invention, the fan-shaped piece is provided with a convex column between the circular arc end and the top end, the base is provided with a travel slot matched with the convex column, the travel slot is arc-shaped.

As a preferred embodiment of the present invention, the fan-shaped piece is provided with a roller matched with the convex column, the roller is mounted on the convex column to achieve that the convex column is fixed in the travel slot, the roller can rotate around the convex column.

As a preferred embodiment of the present invention, a secondary travel slot is provided around the travel slot, the roller is fixed in the secondary travel.

As a preferred embodiment of the present invention, a sensor is provided on the limiting blocks, when the blocking block abutting against the limiting blocks, the sensor sends out a signal to control the motor stop working.

As a preferred embodiment of the present invention, the filter is located between the convex column and the circular arc end.

As a preferred embodiment of the present invention, the scanning lens comprises scanning single lens and scanning balsaming lens, the scanning balsaming lens comprises plano-convex lens and plano-concave lens.

Compared with the prior art, the benefits of the prevent invention as follows: compared with the prior art, the confocal laser fundus angiographic device is capable of automatically switching the filter, thereby avoiding the problem of forgetting to switch the filter due to the operator's mistake or switching the filter by mistake.

DESCRIPTION OF EMBODIMENTS

Figure 1:
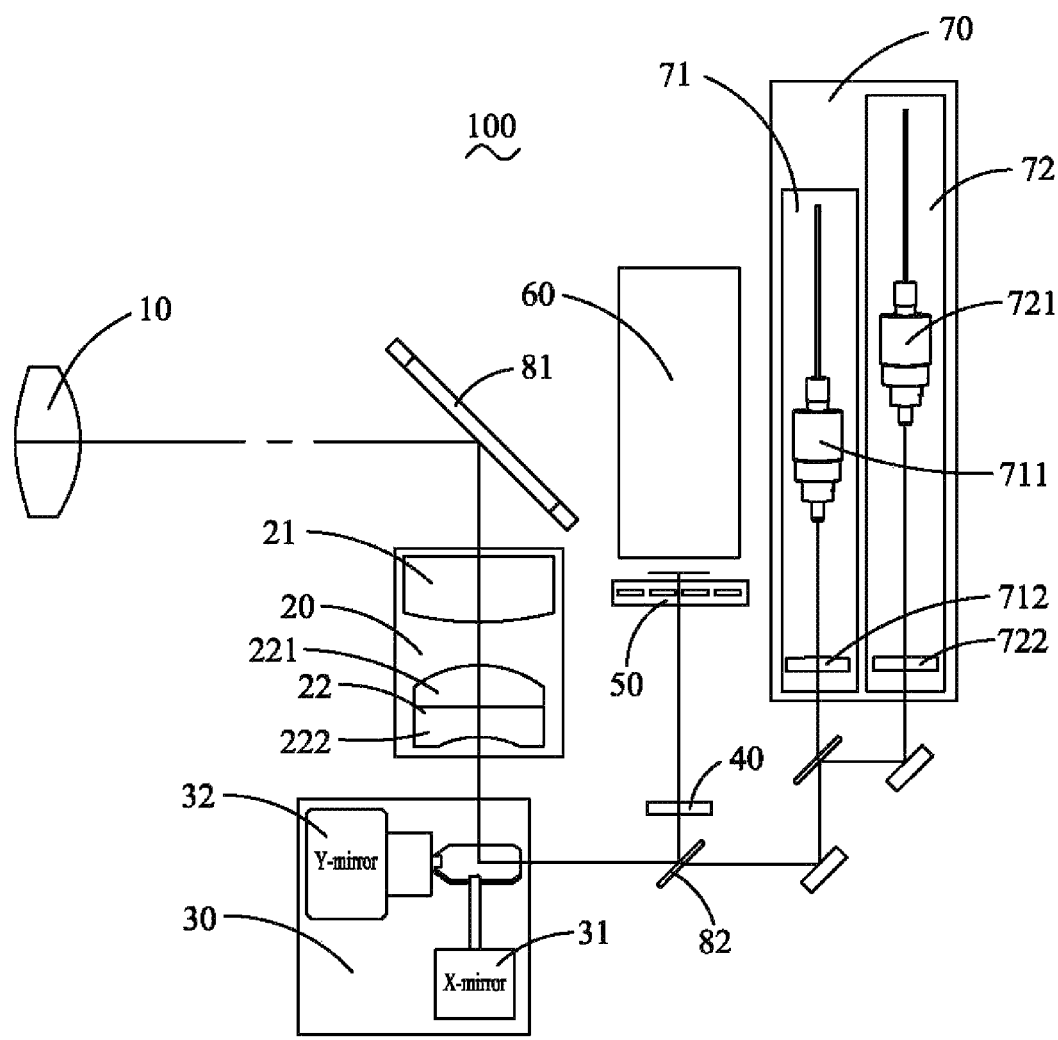
FIG. 1 is a schematic view of a confocal laser fundus angiographic device of the present invention.
Figure 2:
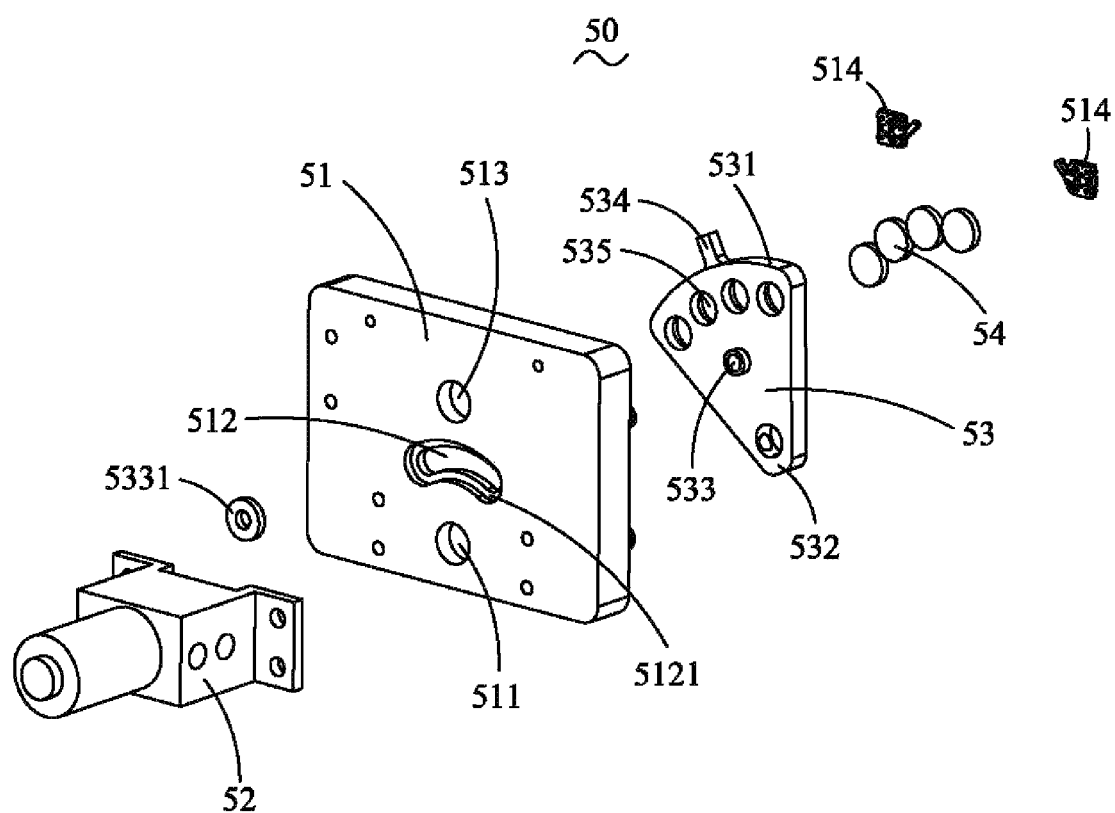
FIG. 2 is a partially exploded, schematic view of a filtering module.
Figure 3:
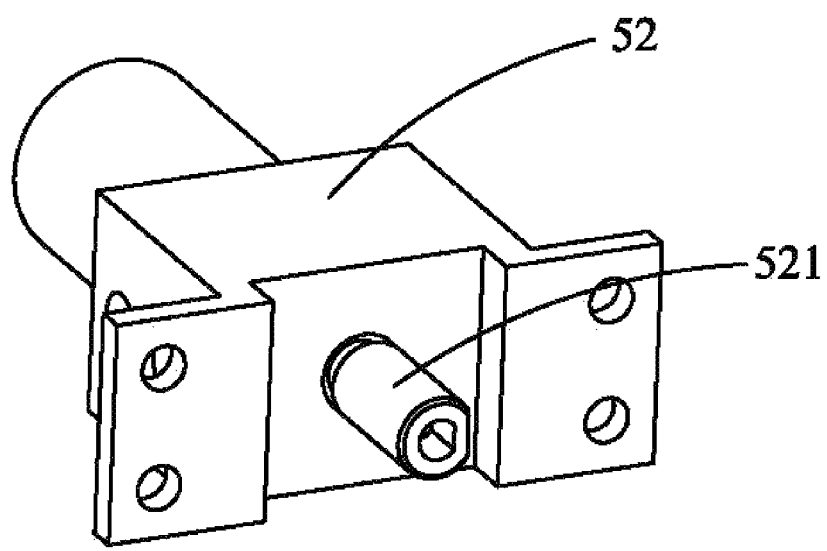
FIG. 3 is a schematic view of a motor.
Figure 4:
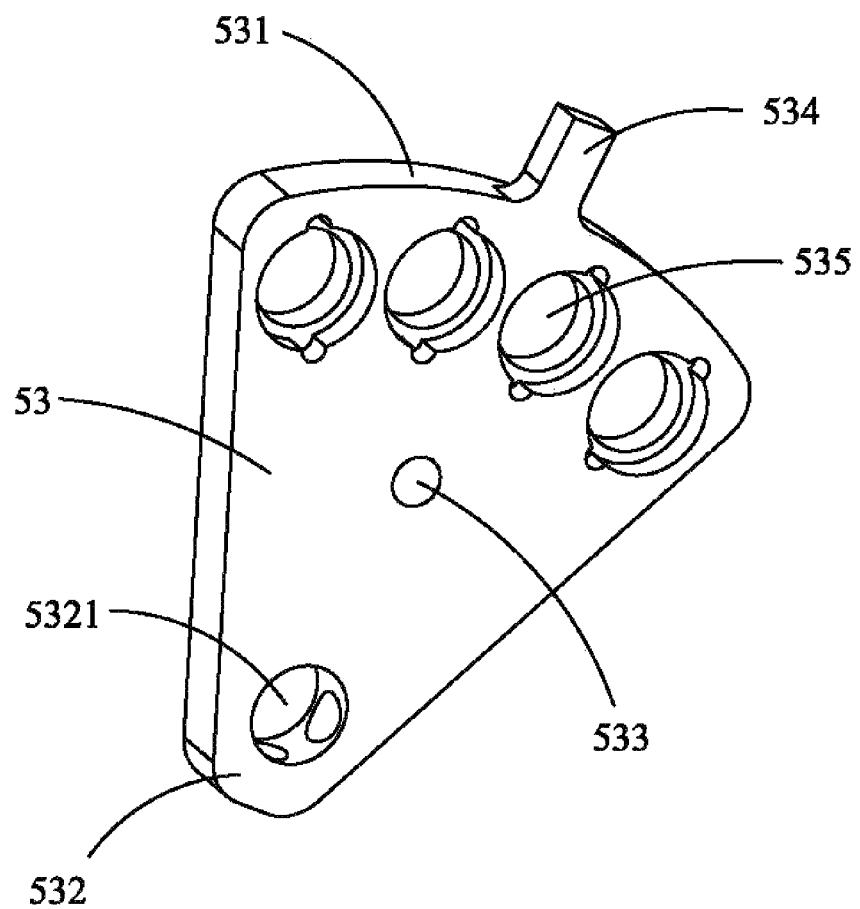
FIG. 4 is a schematic view of a rotary block.
Figure 5:
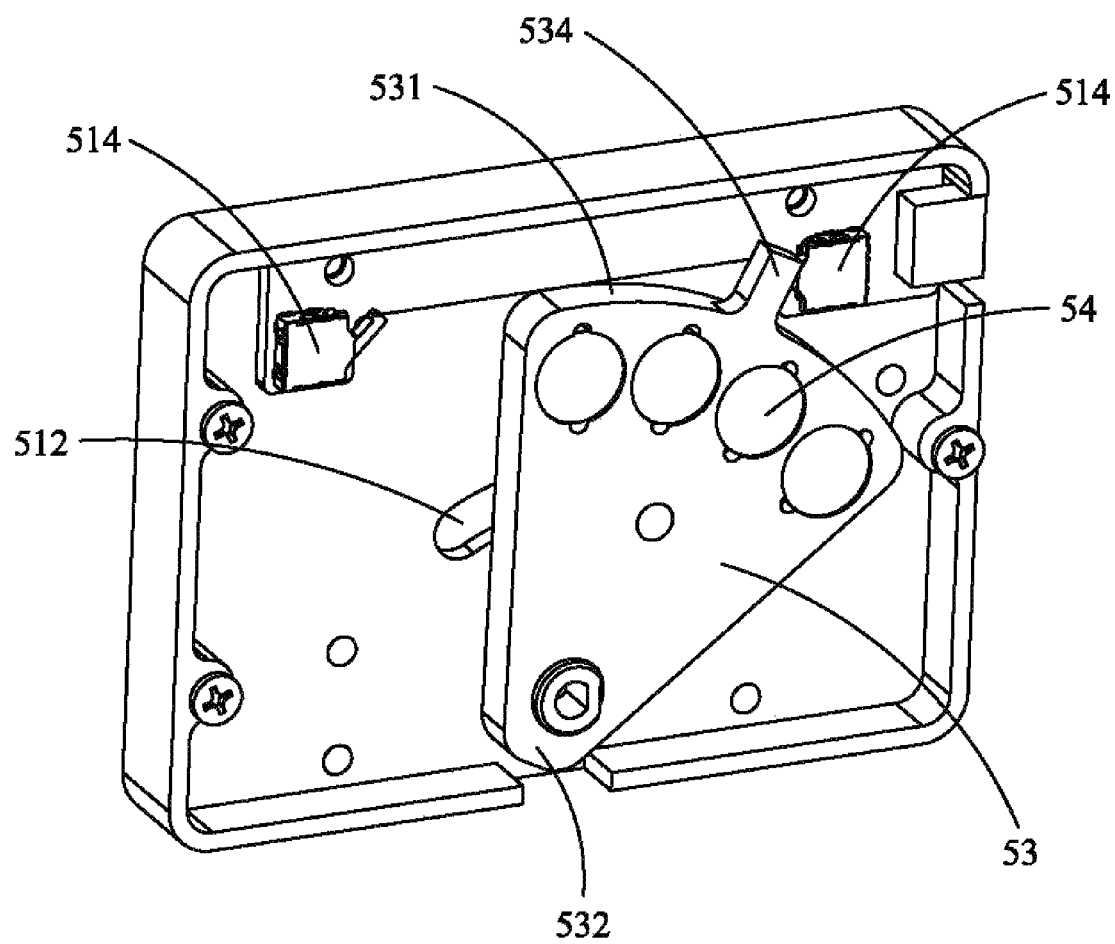
FIG. 5 is another schematic view of the rotary block.

In order to clear the purpose, the technical scheme and the advantages of the invention, reference will now be made to the drawing figures to describe the embodiments of the present disclosure in detail.

Referring to FIG. 1, the present invention discloses a confocal laser fundus angiographic device 100 comprises an objective lens 10, a scanning lens 20, a scanning galvanometer 30, a mirror 40, a filtering module 50, an imaging detection assembly 60 and excitation light source 70. The excitation light source 70 emits illumination light passes through the scanning galvanometer 30, the scanning lens 20, the objective lens 10, and then enters in the fundus, the fluorescent substances in the fundus vein are excited by the illumination light to emit light with a specific wavelength, the specific wavelength light passes through the objective lens 10, the scanning lens 20, the scanning galvanometer 30, the mirror 40, the filtering module 50, and then enters in the imaging detection assembly 60.

Referring to FIG. 1, the objective lens 10 is double aspheric mirrors. The scanning lens 20 comprises scanning single lens 21 and scanning balsaming lens 22; the scanning balsaming lens 22 comprises a first lens 221 and a second lens 222 adhered to the first lens 221. The scanning single lens 21 and the first lens 221 are plano-convex lens, the second lens 222 is plano-concave lens. The scanning single lens 21 cooperates with the scanning balsaming lens 22 to eliminate stray light effectively. Further, there is a reflective mirror 81 disposed between the objective lens 10 and the scanning lens 20, the reflective mirror 81 can change the transmission path of the light. The scanning galvanometer 30 comprises an X-axis scanning galvanometer 31 and a Y-axis scanning galvanometer 32. The mirror 40 is located between the scanning galvanometer 30 and the filtering module 50. In this embodiment, the mirror 40 is a plano-convex lens. A dichroic mirror 82 is further disposed between the scanning galvanometer 30 and the mirror 40.

Referring to FIGS. 2-5, the filtering module 50 comprises a base 51, a motor 52 mounted on the base 51, a rotary block 53 mounted on the motor 52, and at least one piece of filter 54 mounted on the rotary block 53. The base 51 is provided with a through hole 511 matched with the motor 52, a travel slot 512 and a light-through hole 513 matched with the rotary block 53 and a pair of limiting blocks 514, the travel slot 512 is arc-shaped. The motor 52 has an output shaft 521, the output shaft 521 passes through the through hole 511. The rotary block 53 is a fan-shaped piece, the fan-shaped piece comprising a circular arc end 531 and a top end 532 opposite to the circular arc end 531. The top end 532 is provided with a mounting hole 5321, the rotary block 53 is mounted on the output shaft 521 of the motor 52 through the mounting hole 5321. The fan-shaped piece is provided with a convex column 533 and a roller 5331 matched with the convex column 533, the convex column 533 is located between the circular arc end 531 and the top end 532. The convex column 533 matched with the travel slot 512 to achieve that limit a rotation angle of the rotary block 53; the roller 5331 is mounted on the convex column 533 to achieve that the convex column 533 is fixed in the travel slot 512 and prevent the convex column 533 from breaking away from the travel slot 512. The rotary block 53 and the roller 5331 are located at different side of the travel slot 512 respectively. The roller 5331 can rotate around the convex column 533, thereby when the rotary block 53 rotating, reducing the resistance. A secondary travel slot 5121 is provided around the travel slot 512, the roller 5331 is fixed in the secondary travel 5121. A blocking block 534 is formed on an outer side of the circular arc end 531 facing away from the top end 532, the blocking block 534 cooperates with the limiting blocks 514 to limit a rotation angle of the rotary block 53. A sensor (not illustrated) is provided on the limiting blocks 514. When the blocking block 534 abutting against the limiting blocks 514, the sensor sends out a signal to control the motor 52 stop working, thereby preventing the motor 52 from rotating excessively, avoiding that the motor 52 and the rotary block 53 are damaged. The rotary block 53 is provided with a mounting groove 535 between the convex column 533 and the circular arc end 531, the filter 54 is mounted in the mounting groove 535.

Referring to FIG. 1, the excitation light source 70 comprises a first excitation light source 71 and a second excitation light source 72. The first excitation light source 71 comprises a first laser light source 711 and a first collimator lens 712. The wavelength of the first laser light source 711 is 785 nanometers. The second excitation light source 72 comprises a second laser light source 721 and a second collimator lens 722. The wavelength of the second laser light source 721 is 488 nanometers.

When the confocal laser fundus angiographic device 100 in operation, first, open the excitation light source 70, the excitation light source emits illumination light successively passes through the scanning galvanometer 30, the scanning lens 20, the objective lens 10, and then enters in the fundus, the fluorescent substances in the fundus vein are excited by the illumination light to emit light with a specific wavelength, the light with the specific wavelength successively passes through the objective lens 10, the scanning lens 20, the scanning galvanometer 30, the mirror 40, the filtering module 50, and then enters in the imaging detection assembly 60. In the embodiment, the filtering module 50 contains four pieces of filter. When the operator willing to switch the imaging mode among sodium fluorescein angiography, indocyanine green angiography, infrared fundus imaging, fundus self-fluorescence and so on, only need to press the button corresponding to the different imaging modes, the rotary block 53 rotating under the driving of the motor 52 to achieve that corresponding filter 54 and the light-through hole 513 coincide.

Compared with the prior art, the present invention confocal laser fundus angiographic device 100 is capable of automatically switching the filter 54, thereby avoiding the problem of forgetting to switch the filter 54 due to the operator's mistake or switching the filter 54 by mistake.

It is to be understood, for the general technical personnel in this field, the equivalent changes made for the invention under the guidance of the present invention should still be included in the scope advocated by the patent application scope of the invention.

What is claimed is:

1. A confocal laser fundus angiographic device, wherein the device comprises an objective lens, a scanning lens, a scanning galvanometer, a mirror, a filtering module, an imaging detection assembly, and an excitation light source, said excitation light source emits illumination light passing through said scanning galvanometer, said scanning lens, said objective lens, and then entering in the fundus, the fluorescent substances in the fundus vein are excited by the illumination light to emit light with a specific wavelength, said light with the specific wavelength passes through said objective lens, said scanning lens, said scanning galvanometer, said mirror, said filtering module, and then enters in said imaging detection assembly, wherein said filtering module comprising a base, a motor mounted on said base, a rotary block mounted on said motor, and at least one piece of filter mounted on said rotary block, said base is provided with a light-through hole, said rotary block is a fan-shaped piece, said fan-shaped piece comprising a circular arc end and a top end, said top end opposite to said circular arc end and it is provided with a mounting hole, said rotary block is mounted on said motor through said mounting hole, a blocking block is formed on outer side of said circular arc end facing away from said top end, a pair of limiting blocks are disposed on said base, said blocking block cooperates with said limiting blocks to limit a rotation angle of said rotary block, when said confocal laser fundus angiographic device in operation, said rotary block rotating under the driving of said motor to achieve that said filter and said light-through hole coincide.

2. The confocal laser fundus angiographic device according to claim 1, wherein said fan-shaped piece is provided with a convex column between said circular arc end and said top end, said base is provided with a travel slot matched with said convex column, said travel slot is arc-shaped.

3. The confocal laser fundus angiographic device according to claim 2, wherein said fan-shaped piece is provided with a roller matched with said convex column, said roller is mounted on said convex column to achieve that said convex column is fixed in said travel slot, said roller can rotate around said convex column.

4. The confocal laser fundus angiographic device according to claim 3, wherein a secondary travel slot is provided around said travel slot, said roller is fixed in said secondary travel.

5. The confocal laser fundus angiographic device according to claim 1, wherein a sensor is provided on said limiting blocks, when said blocking block abutting against said limiting blocks, said sensor sends out a signal to control said motor stop working.

6. The confocal laser fundus angiographic device according to claim 2, wherein said filter is located between said convex column and said circular arc end.

7. The confocal laser fundus angiographic device according to claim 1, wherein said scanning lens comprises scanning single lens and scanning balsaming lens, said scanning balsaming lens comprises plano-convex lens and plano-concave lens.

8. A confocal laser fundus angiographic device comprising:
   an illumination optical means for illumination an eye fundus; and
   a photographing optical means for photographing an image of the illuminated eye fundus, said photographing optical means comprising:
   an imaging detection assembly; and
   a filtering module co-working with said imaging detection assembly, said filter module comprising a base defining a light-through hole, a motor mounted on said base, a fan-shaped rotary block mounted on said motor, and a plurality of filters mounted and positioned on said fan-shaped rotary block along an arching line, said base having a pair of limiting blocks, wherein said fan-shaped rotary block is configured to be rotatable between said pair of limiting blocks of said base to thereby align one of said plurality of filters with said light-through hole of said base.

9. The device as claimed in claim 8, wherein said illumination optical means comprises an objective lens, a scanning lens, a scanning galvanometer, a mirror, and an excitation light source.

10. The device as claimed in claim 8, wherein the fan-shaped rotary block is provided with a mounting hole, by which said fan-shaped rotary block is mounted on said motor, and a blocking block formed to cooperate with said pair of limiting blocks to limit a rotation angle of said fan-shaped rotary block.

11. The device as claimed in claim 10, wherein said fan-shaped piece has a circular arc end and a top end, said top end being opposite to said circular arc end and provided with said mounting hole therethrough.

12. The device as claimed in claim 11, wherein said blocking block is formed on outer side of said circular arc end facing away from said top end.

* * * * *